United States Patent
Lv et al.

(10) Patent No.: US 12,343,251 B2
(45) Date of Patent: Jul. 1, 2025

(54) CONTROLLABLE GUIDING DEVICE FOR IMPLANTABLE APPARATUS

(71) Applicant: Jenscare Scientific Co., Ltd., Zhejiang (CN)

(72) Inventors: Shiwen Lv, Ningbo (CN); Zhi Chen, Ningbo (CN); Jin Xu, Ningbo (CN)

(73) Assignee: Jenscare Scientific Co., Ltd., Zhejiang (CN)

(*) Notice: Subject to any disclaimer, the term of this patent is extended or adjusted under 35 U.S.C. 154(b) by 655 days.

(21) Appl. No.: 17/786,311

(22) PCT Filed: Dec. 15, 2020

(86) PCT No.: PCT/CN2020/136450
§ 371 (c)(1),
(2) Date: Jul. 1, 2022

(87) PCT Pub. No.: WO2021/121214
PCT Pub. Date: Jun. 24, 2021

(65) Prior Publication Data
US 2023/0024606 A1 Jan. 26, 2023

(30) Foreign Application Priority Data
Dec. 17, 2019 (CN) .......................... 201911299139.X (51) Int. Cl.
*A61M 25/01* (2006.01)
*A61F 2/24* (2006.01)
*A61F 2/95* (2013.01)

(52) U.S. Cl.
CPC .............. *A61F 2/24* (2013.01); *A61F 2/2427* (2013.01); *A61F 2/95* (2013.01); *A61M 25/0136* (2013.01);
(Continued)

(58) Field of Classification Search
CPC ......... A61M 2025/015; A61M 25/0147; A61F 2/2427; A61F 2/2466; A61F 2/2439; A61F 2/95; A61F 2002/9511
See application file for complete search history.

(56) References Cited

U.S. PATENT DOCUMENTS

2013/0197629 A1  8/2013  Gainor et al.
2014/0107758 A1  4/2014  Glazier
(Continued)

FOREIGN PATENT DOCUMENTS

CN    104055600 A    9/2014
CN    104055601 A    9/2014
(Continued)

OTHER PUBLICATIONS

International Search Report dated Mar. 22, 2021 issued in corresponding Parent Application No. PCT/CN2020/136450 w/English Translation, 6 pages.
(Continued)

Primary Examiner — Dinah Baria
(74) Attorney, Agent, or Firm — Wood, Phillips, Katz, Clark & Mortimer (57) ABSTRACT

A guiding device is provided. An implantable apparatus includes a member to be anchored. A position-limiting wire is detachably connected to the implantable apparatus. A proximal end of the position-limiting wire is connected to the control handle. A distal end of the guiding catheter is provided with a guiding member. A distal end portion of the guiding catheter is bendable. A proximal end of the delivery catheter and a proximal end of the guiding catheter are respectively connected to the control handle. When the control handle is manipulated to make the guiding member on the guiding catheter move along the position-limiting wire toward the distal end, the distal end portion of the guiding catheter is bent and deformed, such that the distal
(Continued)

end of the guiding catheter abuts against the member to be anchored of the implantable apparatus.

15 Claims, 6 Drawing Sheets

(52) U.S. Cl.
CPC ........ *A61F 2/2466* (2013.01); *A61M 25/0147* (2013.01); *A61M 2025/015* (2013.01)

(56) References Cited

U.S. PATENT DOCUMENTS

| | | | |
|---|---|---|---|
| 2016/0113765 A1 | 4/2016 | Ganesan et al. | |
| 2018/0228608 A1 | 8/2018 | Sheps et al. | |

FOREIGN PATENT DOCUMENTS

| | | | |
|---|---|---|---|
| CN | 104055602 | A | 9/2014 |
| CN | 104055603 | A | 9/2014 |
| CN | 104055604 | A | 9/2014 |
| CN | 104055601 | B | 8/2016 |
| CN | 107249482 | A | 10/2017 |
| CN | 110292464 | A | 10/2019 |
| CN | 111035474 | A | 4/2020 |
| CN | 111067666 | A | 4/2020 |
| CN | 211583671 | U | 9/2020 |
| CN | 211723549 | U | 10/2020 |

OTHER PUBLICATIONS

First Office Action for Chinese Application No. 201911299139.X issued Mar. 31, 2023.
Second Office Action for Chinese Application No. 201911299139.X mailed Aug. 17, 2023.
European Supplementary European Search Report for Application No. EP 20 90 4036 mailed Dec. 19, 2022.

CONTROLLABLE GUIDING DEVICE FOR IMPLANTABLE APPARATUS

CROSS-REFERENCE TO RELATED APPLICATION

This application is a National Phase of International Application No. PCT/CN2020/136450 filed on Dec. 15, 2020 which claims the priority of the Chinese Patent filed on Dec. 17, 2019 with the application number 201911299139.X and entitled "A Controllable Guiding Device for Implantable Devices", which is hereby incorporated by reference in their entireties.

FIELD

This present application relates to a medical apparatus, and in particular to a controllable guiding device for an implantable apparatus.

BACKGROUND

Minimally invasive transcatheter treatment has gradually become a main treatment measure for cardiovascular diseases. A cardiovascular implantable apparatus such as a coronary stent, a heart valve, an occlusion device, a great vessel stent, or the like needs to be delivered to a desired position in the human body through a delivery device. The implantable apparatus needs to be fixed to the target position, and the fixation of the prosthetic heart valve is particularly important. In traditional technology, the fixations of an aortic valve and a pulmonary valve mainly rely on radial support force of the valve stent. The valve stent is provided with a clamping member, a protrusion, a recess, or the like, taking advantage of shape and characteristics of the anatomical structure to realize the fixation. To achieve the fixations of a mitral valve leaflet and a tricuspid valve leaflet, auxiliary fixation devices, such as, barbs, hooks, leaflet clamps, annulus clamps, heart apical fixation wires, and heart apical fixation rods, are often provided in addition to the radial support force. However, due to the complex anatomical structures of the mitral valve and the tricuspid valve, if the fixations only rely on the radial support of the valve stent and the auxiliary fixation devices, on the one hand, the native valve annulus will be greatly affected, hindering the diastolic and systolic movements of the heart, which is not a satisfactory solution for the fixation problem, and on the other hand, for minimally invasive transcatheter products, limited by the diameter and the performance of the catheter, it is difficult to provide an effective and relatively flexible structure in the implantable apparatus for fixing to the target anatomical structure.

Patent CN 201410316922.3 describes a repair system for preventing valve regurgitation with an anchoring device. An anchor-releasing device includes a delivery tube and a push rod. The anchor-releasing device and a fixing unit are detachably connected. The distal end portion of the anchor-releasing device has a preset shape such that the distal end portion of the delivery tube can be bent overall or partially to facilitate the most distal end of the delivery tube abutting against the fixation unit or an autologous tissue before the anchor is moved. In this solution, the detachable connection operation between the anchor-releasing device and the fixing unit is relatively complicated, requiring high precision and being difficult for assemblage. Moreover, after the sheath is retracted, the detachable connection position has a large stress, which is easy to damage the implantable apparatus and the anchor-releasing device. Before anchoring, the bending degree of the delivery tube needs to be fixed by a support structure, and otherwise the distal end of the delivery tube is difficult to abut against the fixing unit. In the process of retracting and releasing the sheath, as the length of the delivery tube changes, a gap may exist between the distal end of the delivery tube and the fixed unit before anchoring, resulting unstable attachment, which will affect the anchoring effect and cause a high-risk surgery. For the implantable apparatus that requires fixation at multiple points, this solution requires multiple delivery tubes, rendering a more complicated structure, and increasing the diameter of the delivery tube. Moreover, it is not possible to re-anchor when the anchoring operation is finished, and the surgical risk is high.

SUMMARY

A controllable guiding device for an implantable apparatus includes the implantable apparatus, a delivery catheter, and a control handle, and further includes a guiding catheter and a position-limiting wire. The implantable apparatus includes a member to be anchored. The position-limiting wire is detachably connected to the implantable apparatus. A proximal end of the position-limiting wire is connected to the control handle. A distal end of the guiding catheter is provided with a guiding member. A distal end portion of the guiding catheter is bendable. A proximal end of the delivery catheter and a proximal end of the guiding catheter are respectively connected to the control handle. In an assembled state, the guiding catheter and the position-limiting wire are placed in the delivery catheter, and the position-limiting wire extends through the guiding member. On a condition that the control handle is manipulated to make the guiding member on the guiding catheter move along the position-limiting wire toward the distal end, the distal end portion of the guiding catheter is bent and deformed, such that the distal end of the guiding catheter abuts against the member to be anchored of the implantable apparatus.

In an embodiment, the controllable guiding device for the implantable apparatus further includes an anchor and an anchor push member. In the assembled state, the anchor and the anchor push member are placed in the guiding catheter. On a condition that the anchor push member pushes the anchor, the anchor moves toward the distal end to anchor the member to be anchored of the implantable apparatus to the target tissue.

In an embodiment, the controllable guiding device for the implantable apparatus further includes a control rod. The distal end of the position-limiting wire has a locking ring. The implantable apparatus includes a connecting ring. A proximal end of the control rod is connected to the control handle. In the assembled state, the locking ring passes through the connecting ring of the implantable apparatus, and then the distal end of the control rod is inserted into the locking ring. On a condition that the control handle is manipulated to tighten and lock the position-limiting wire, a connection is formed between the implantable apparatus, the position-limiting wire, the control rod, and the guiding catheter, thereby fixing the relative position therebetween. On a condition that the control handle is manipulated to axially move the control rod, such that the distal end of the control rod is disengaged from the locking ring, the implantable apparatus is releasable from the position-limiting wire.

In an embodiment, a distal end of the control rod is a detach-preventing end, and the detach-preventing end is an inverted conical structure, a Y-shaped structure, a wave-shaped structure, or a compressible round structure.

In an embodiment, the locking ring at the distal end of the position-limiting wire is a compressible round structure or a U-shaped ring formed from multiple folded wires.

In an embodiment, the guiding member is fixedly connected to the guiding catheter. The guiding member is located at the distal end of the guiding catheter. The guiding member includes a guiding hole. In the assembled state, the distal end of the position-limiting wire first extends through the guiding hole, and then extends through the connecting ring.

In an embodiment, the guiding member and the guiding catheter are integrated together as one piece.

In an embodiment, the control rod extends through the guiding hole in the guiding member.

In an embodiment, the guiding member is fixedly connected to the distal end of the control rod, and the guiding member includes a guiding hole. In the assembled state, the distal end of the position-limiting wire first passes through the guiding hole, and then passes through the connecting ring.

In an embodiment, the guiding catheter passes through the guiding hole in the guiding member.

In an embodiment, the member to be anchored is integrated with the implantable apparatus.

In an embodiment, the member to be anchored is a flexible piece. One end of the member to be anchored is connected to the implantable apparatus. In an embodiment, the flexible piece is deformable and made of soft material.

In an embodiment, the member to be anchored includes a support mesh.

In an embodiment, the implantable apparatus includes a frame, and the member to be anchored is disposed on the frame.

Compared with the traditional technology, the advantages of the embodiments of the present application are as follows:
1. The structure is simple and the operation is convenient. One position-limiting wire can play multiple functions such as guiding, bending, positioning, and pulling, and is detachable.
2. The position-limiting wire acts as a guide rail to guide and restrict moving of the guiding catheter along a specific direction, which has following advantages: On the one hand, the position requirement of the guiding catheter in assemblage is reduced, the difficulty of assemblage is reduced, and the guiding catheter and the position-limiting wire are movably connected. There is no internal stress between the various parts, reducing damage to the product. On the other hand, if the anchoring position or anchoring effect is not desired, the guiding catheter can be withdrawn from the delivery catheter and reloaded with the anchor, and then a re-anchor operation can be performed along the position-limiting wire, greatly avoiding the surgical risk.
3. The position-limiting wire acts as a bending wire to change the distal end portion of the guiding catheter from the initial straight state to the state having the fixed angle, changing the direction of anchor, which is conducive to achieving a desired anchoring position and simplifies the structure of the delivery device.
4. The position-limiting wire acts as a positioning wire, which is connected to a specific position of the implantable apparatus to accurately control the position of the anchor outlet of the guiding catheter relative to the member to be anchored to achieve precise anchoring.
5. The position-limiting wire acts as a pull wire to offset the interacting force between the anchor and the member to be anchored during the anchoring operation and to ensure that the guiding catheter is in tight contact with the member to be anchored before anchoring of the anchor, ensuring that the anchor safely and effectively fixes the member to be anchored to the target tissue.
5. The position-limiting wire acts as a detachable wire, which can be separated from the implantable apparatus after the anchoring operation is completed.

BRIEF DESCRIPTION OF THE DRAWINGS

To describe the technical solutions in the embodiments of the present application or in the traditional technology more clearly, the following briefly describes the accompanying drawings referred in the description of the embodiments. The accompanying drawings in the following description show merely some embodiments of the present application, and a person of ordinary skill in the art may derive other drawings from the provided accompanying drawings without creative efforts.

DETAILED DESCRIPTION

The technical solutions in the embodiments of the present application will be described clearly and completely in the following with reference to the accompanying drawings in the embodiments of the present application. Apparently, the described embodiments are merely some rather than all of the embodiments of the present application. All other embodiments obtained by one of ordinary skill in the art based on the embodiments of the present application without creative efforts shall fall within the protection scope of the present application.

Unless otherwise defined, all the technical and scientific terms used in this specification have the same meaning as commonly understood by one of ordinary skill in the art to which this application belongs. Additionally, the terms used in the specification of the present application are merely for describing the specific embodiments, and are not intended to limit the present application. As used herein, the term "and/or" includes any and all combinations of one or more of the associated listed items.

The proximal end described in the present application refers to the end nearer to a control handle or an operator, and the distal end described in the present application refers to the end farther from the control handle or the operator.

Example 1

Figure 1:
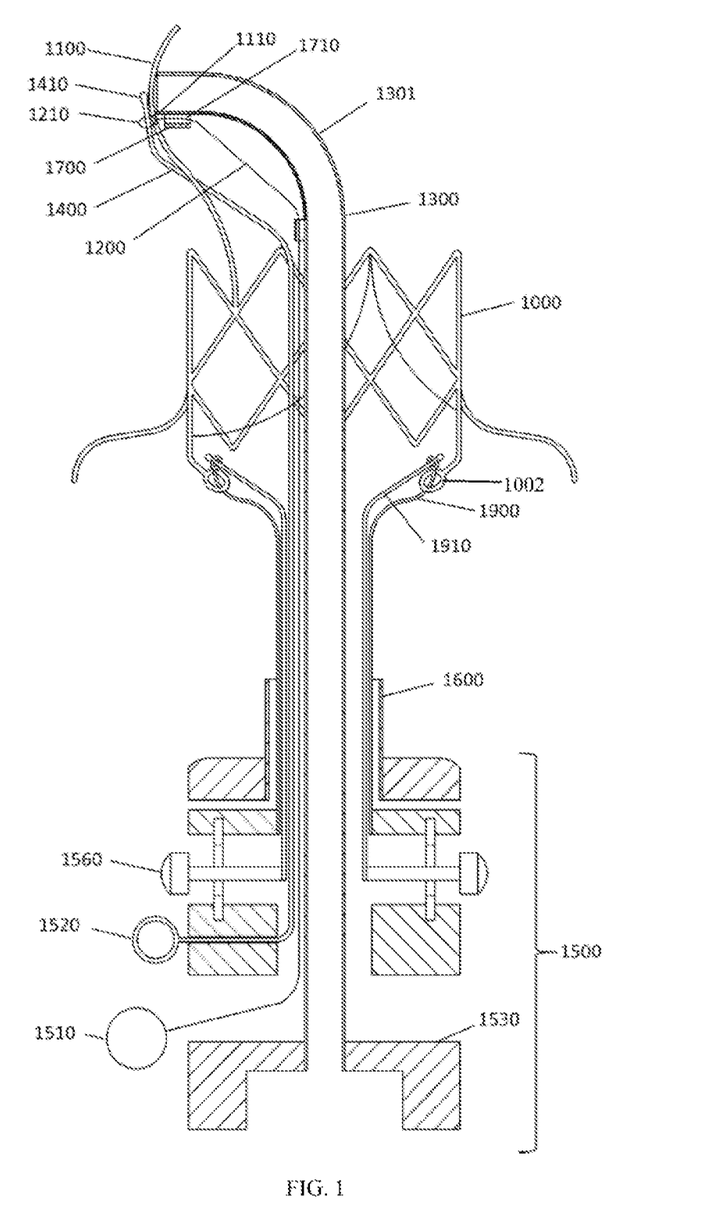
FIG. 1 is a schematic structural view of a controllable guiding device for an implantable apparatus in Example 1 of the present application.
Figure 4A:
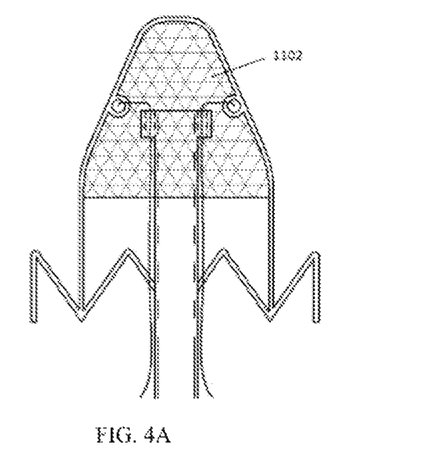
FIG. 4A to FIG. 4D are schematic structural views of various embodiments of a member to be anchored in Example 1 of the present application.
Figure 4B:
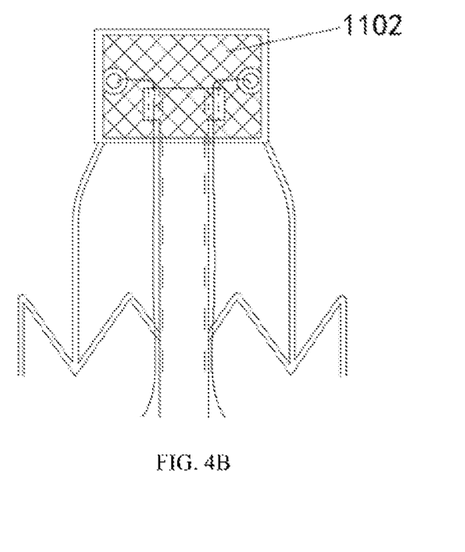
Figure 4C:
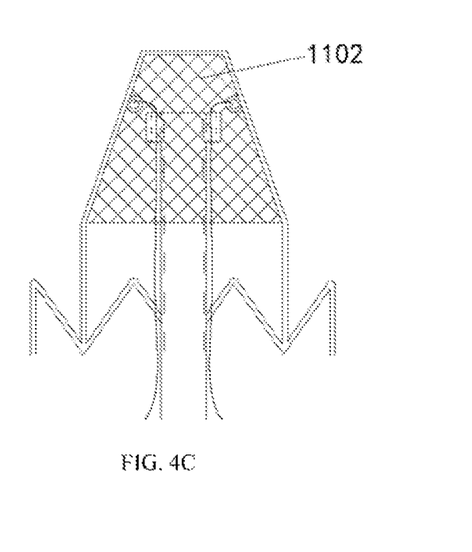
Figure 4D:
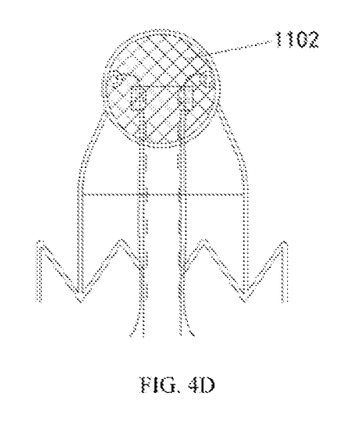

Referring to FIG. 1 and FIG. 4A, a controllable guiding device for an implantable apparatus includes an implantable apparatus 1000, a delivery catheter 1600, a control handle 1500, a guiding catheter 1300, and a position-limiting wire 1200. The implantable apparatus 1000 includes a member to be anchored 1102. The position-limiting wire 1200 is detachably connected to the implantable apparatus 1000. A proximal end of the position-limiting wire 1200 is connected to the control handle 1500. A distal end of the guiding catheter 1300 is provided with a guiding member 1700. A distal end portion of the guiding catheter 1300 is bendable. A proximal end of the delivery catheter 1600 and a proximal end of the guiding catheter 1300 are respectively connected to the control handle 1500. In an assembled state, the guiding catheter 1300 and the position-limiting wire 1200 are placed in the delivery catheter 1600. The position-limiting wire 1200 extends through the guiding member 1700. On a condition that the control handle 1500 is manipulated to make the guiding member 1700 on the guiding catheter 1300 move along the position-limiting wire 1200 toward the distal end, the distal end portion of the guiding catheter 1300 is bent and deformed, such that the distal end of the guiding catheter 1300 abuts against the member to be anchored 1102 of the implantable apparatus 1000.

In an embodiment, under the cooperative movement of the position-limiting wire 1200 and the guiding member 1700, the distal end portion of the guiding catheter 1300 is bent and deformed, and the guiding catheter 1300 during deformation pushes the member to be anchored 1102 of the implantable apparatus 1000, causing the member to be anchored 1102 to move radially toward a target tissue. On a condition that the position-limiting wire 1200 is pulled tight, the distal end portion of the guiding catheter 1300 forms a fixed angle, facilitating the distal end of the guiding catheter 1300 abutting against the member to be anchored 1102, so that the member to be anchored 1102 is attached to the target tissue.

Figure 2:
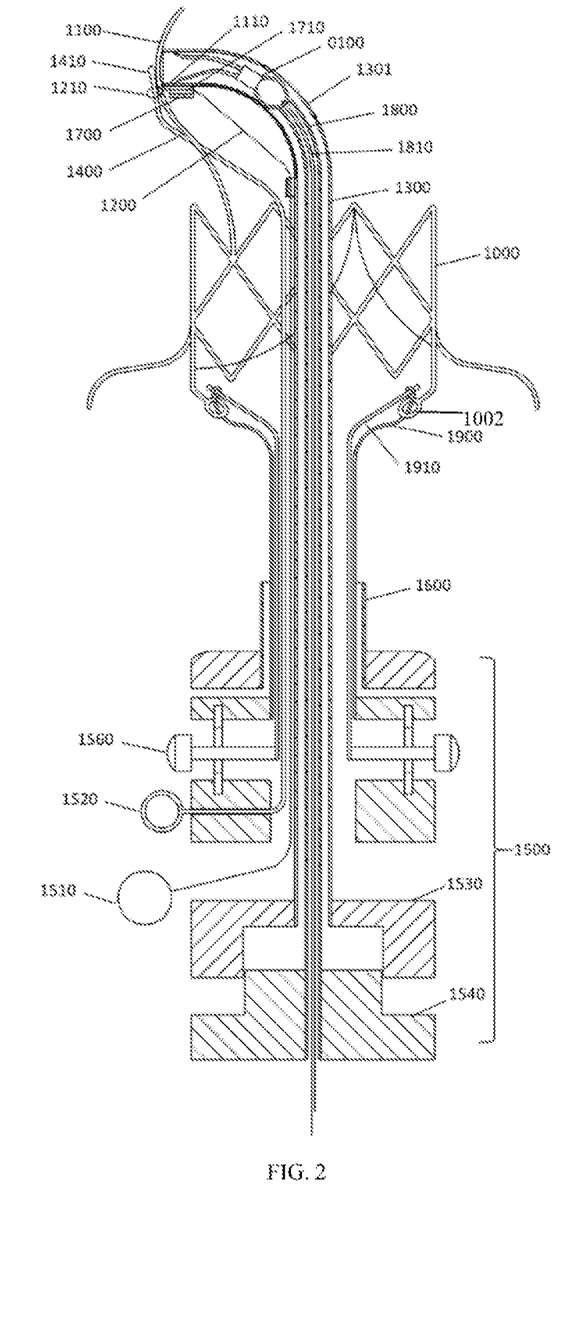
FIG. 2 is a schematic structural view of a controllable guiding device for an implantable apparatus provided with an anchor and an anchor push member in Example 1 of the present application.

Referring to FIG. 2, the controllable guiding device for the implantable apparatus further includes an anchor 0100 and an anchor push member 1800. In the assembled state, the anchor 0100 and the anchor push member 1800 are placed in the guiding catheter 1300. When the anchor push member 1800 pushes the anchor 0100, the anchor 0100 moves toward the distal end to anchor the member to be anchored 1102 of the implantable apparatus 1000 to the target tissue. The implantable apparatus 1000 further includes a plurality of annular coupling ends 1002. A connecting member 1900 and a control member 1910 are also arranged in the delivery catheter 1600. The connecting member 1900 is a rod-shaped structure whose distal end has a ring. The control member 1910 is a hard rod or a hard wire. In the assembled state, the connecting member 1900 first passes through the coupling end 1002, and then a distal end of the control member 1910 passes through the ring of the connecting member 1900. The proximal end of the control member 1910 is fixedly connected to a sixth controller 1560 of the control handle 1500.

Figure 3:
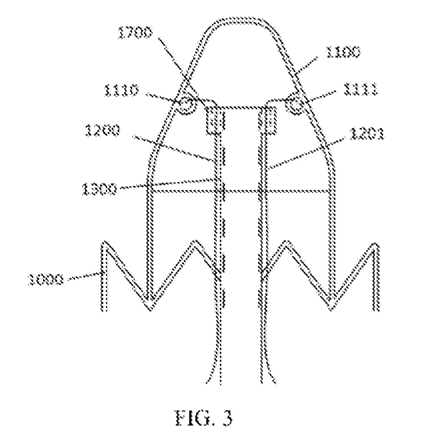
FIG. 3 is a schematic view of an embodiment of a distal end portion of the controllable guiding device for the implantable apparatus in Example 1 of the present application.

Referring to FIG. 3 and FIG. 4A, the implantable apparatus 1000 includes a frame 1100, a connecting ring 1110, and a connecting ring 1111. The frame 1100 is a compressible structure such as a V-shaped or a rhombus compressible structure, and has adequate strength and hardness. The connecting rings 1110 and 1111 are annular structures and are located on the frame 1100. The connecting rings 1110 and 1111 and the frame 1100 are made of nickel-iron tubes which are integrally cut by laser and subjected to heat treatment for shaping. The member to be anchored 1102 is disposed in the space formed by the frame 1100. The member to be anchored 1102 is a flexible piece, such as a polymer fabric. The edge of one end of the member to be anchored 1102 is fixed to the frame 1100 by suture. In an embodiment, the member to be anchored 1102 is a polytetrafluoroethylene (PTFE) material welded to the frame 1100. In another embodiment, the member to be anchored 1102 is integrated with the implantable apparatus 1000. In another embodiment, the member to be anchored 1102 is integrated with the implantable apparatus 1000, and the frame 1100 is integrated with the implantable apparatus 1000. In an embodiment, the member to be anchored 1102 is a flexible member, one end of which is connected to the implantable apparatus 1000, and the member to be anchored 1102 includes a support mesh made of woven metal wires. In another embodiment, the member to be anchored 1102 is a flexible member, one end of which is connected to the implantable apparatus 1000, and the member to be anchored 1102 includes a support mesh made of a polymer network. In another embodiment, the member to be anchored 1102 is a rigid stent made of metal wires. In another embodiment, the member to be anchored 1102 is a support rod. Referring to in FIGS. 4A to 4D, in an embodiment, the member to be anchored 1102 can have a triangle, round, isosceles trapezoid, or rectangular shape. In the present embodiment, the implantable apparatus 1000 is an artificial atrioventricular valve, which is to be fixed to the ventricular wall via the anchor 0100.

In the assembled state, the distal end of the position-limiting wire 1200 is detachably connected to the frame 1100 of the implantable apparatus 1000. The position-limiting wire 1200 is a flexible wire made of polymer material or is a metal wire, which has adequate strength and toughness. The position-limiting wire 1200, when being tightened, can form a relatively robust connection, and, when being loosened, is soft and does not affect the position of other components. The proximal end of the position-limiting wire 1200 is connected to a first controller 1510 of the control handle 1500, as shown in FIG. 1 and FIG. 2.

In an embodiment, referring to FIG. 3, two position-limiting wires 1200, 1201 are arranged in the controllable guiding device for the implantable apparatus, and two guiding members 1700 are symmetrically arranged at the distal end of the guiding catheter 1300. The two position-limiting wires 1200, 1201 respectively extend through the two guiding members 1700, so that the distal end of the single guiding catheter 1300 is connected to both the position-limiting wire 1200 and the second position-limiting wire 1201. When the two position-limiting wires 1200, 1201 are tightened, the distal end of the guiding catheter 1300 can be self-positioned to the midline of the member to be anchored 1102 under the action of the two guiding members 1700, reducing the influence of the frame 1100, the member to be anchored 1102, and detachable points on the outlet end of the guiding catheter 1300. In an embodiment, one guiding catheter 1300 can be connected to two or more position-limiting wires 1200, 1201 at the same time, and the position of the end of the guiding catheter 1300 can be correspondingly positioned by controlling the lengths of different position-limiting wires 1200, 1201.

The guiding member 1700 is fixedly connected to the guiding catheter 1300. The guiding member 1700 is located at the distal end of the guiding catheter 1300. One, two, or more guiding holes 1710 are located in the guiding member 1700. In the assembled state, the distal end of the position-limiting wire 1200 first extends through the guiding hole 1710 and then extends through the connecting ring 1110. The guiding member 1700 has an adequate strength and is made of a metal material or a hard polymer material. The surface of the guiding member 1700 is mechanically polished and smooth without sharp edges to prevent damaging autologous tissues. In an embodiment, the guiding member 1700 and the guiding catheter 1300 are integrated together as one piece, and the distal end portion of the guiding catheter 1300 is a bendable structure. The distal end portion of the guiding catheter 1300 can be formed from a catheter-grade nickel-titanium or stainless steel tube with good elasticity, which is laser engraved to form slits thereon. The head of the slit tube is without slits for a length of 2 mm to 10 mm, preventing the head of the anchor 0100 from getting stuck when being pushed out. The slit tube has an adequate strength and a wall thickness of more than 0.1 mm. The distal end of the guiding catheter 1300 is fixedly connected to the guiding member 1700 through interference fit, welding, or gluing. The proximal end of the guiding catheter 1300 is connected to a third controller 1530 of the control handle 1500. By operating the control handle 1500, the third controller 1530 can drive the guiding catheter 1300 to move in the axial direction.

In another embodiment, the controllable guiding device for the implantable apparatus further includes a control rod 1400. A proximal end of the control rod 1400 is connected to a second controller 1520 of the control handle 1500. The control rod 1400 is a thin rod with an adequate toughness, not easy to have a small-range deformation, and made of metal or memory alloy material. A distal end of the control rod 1400 is a detach-preventing end 1410. The detach-preventing end 1410 can be such as an inverted conical structure, a Y-shaped structure, a wave-shaped structure, or a compressible round structure, preventing accidental disengagement of the distal end of the control rod 1400 from a locking ring 1210. The guiding member 1700 is fixedly connected to the distal end of the guiding catheter 1300, and the guiding member 1700 includes two guiding holes 1710. The distal end of the position-limiting wire 1200 passes through one guiding hole 1710, and the distal end of the control rod 1400 extends through the other one guiding hole 1710. The guiding holes 1710 regulate the moving directions of the position-limiting wire 1200 and the control rod 1400. In an embodiment, the guiding member 1700 is fixedly connected to the distal end of the control rod 1400, and the guiding member 1700 includes two guiding holes 1710. In the assembled state, the distal end of the position-limiting wire 1200 first extends through one guiding hole 1710, and then extends through the connecting ring 1110. The guiding catheter 1300 extends through the other guiding hole, and the guiding member 1700 is movably connected to the guiding catheter 1300, so that the guiding member 1700 can control the moving direction of the guiding catheter 1300. Referring to FIG. 1 and FIG. 2, in an embodiment, the distal end of the position-limiting wire 1200 has a locking ring 1210. In the assembled state, the locking ring 1210 first extends through the guiding hole 1710 of the guiding member 1700, and then extends through the connecting ring 1110 of the implantable apparatus 1000, and then the distal end of the control rod 1400 is inserted into the locking ring 1210, so that a detachable connection is formed between the position-limiting wire 1200, the implantable apparatus 1000, and the control rod 1400. When the control handle 1500 is manipulated to tighten and lock the position-limiting wire 1200, a connection is formed between the implantable apparatus 1000, the position-limiting wire 1200, the control rod 1400, and the guiding catheter 1300, so that the relative position between them is fixed. When the second controller 1520 is manipulated to axially move the control rod 1400, such that the distal end 1410 of the control rod 1400 is disengaged from the locking ring 1210, the implantable apparatus 1000 is releasable from the position-limiting wire 1200. A detachable movable connection is formed between the control rod 1400, the implantable apparatus 1000, the position-limiting wire 1200, and the guiding member 1700. In the assembled state, the position-limiting wire 1200 is movable in a relatively large extent, which is convenient for operation and reduces the difficulty of assembling the implantable apparatus 1000. After assembled into the delivery catheter 1600, the implantable apparatus 1000 and the controllable release device are movably connected, and there is appropriate movement space for the various parts, reducing the internal stress and preventing damage to the product. In an embodiment, the guiding member 1700 is movably connected to the control rod 1400, and the control rod 1400 first extends through the guiding member 1700 and then extends through the locking ring 1210 of the position-limiting wire 1200. The locking ring 1210 is a flexible and compressible structure, which facilitates fast and safe withdrawal from the connecting ring 1110 of the implantable apparatus 1000, and does not affect the position of the implantable apparatus 1000. In an embodiment, the position-limiting wire 1200 and the locking ring 1210 is an integrated structure. The end of the position-limiting wire 1200 is folded in half to form a U-shaped locking ring, or the position-limiting wire 1200 is folded in half and the head thereof is wrapped and braided to form a locking ring. The proximal end of the position-limiting wire 1200 is connected to the first controller 1510 of the control handle 1500. When the control handle 1500 is operated, the first controller 1510 can be moved axially and fixed at a stop position.

Figure 5:
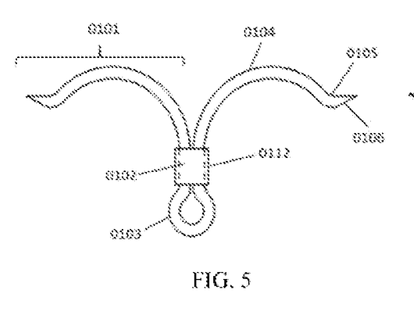
FIG. 5 and FIG. 6 are schematic views of two embodiments of an anchor of the controllable guiding device for the implantable apparatus of the present application.
Figure 6:
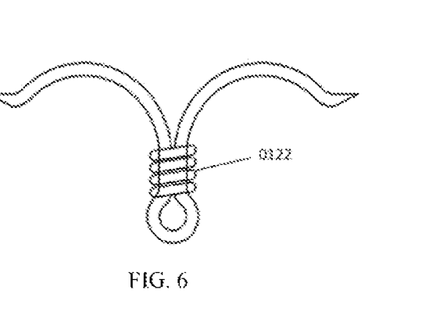

Referring to FIG. 5, the anchor 0100 includes at least one curved needle 0101 and a fixation end 0102 of the curved needle. A distal end of the curved needle 0101 can radially expand to form a curved portion 0104 on the condition that the distal end of the curved needle 0101 is not subject to a force. In the assembled state, the anchor 0100 can be deformed and installed into the lumen of the guiding catheter 1300. When being released from the guiding catheter 1300, the anchor 0100 can restore the preset shape. The curved needle 0101 is a nickel-titanium alloy wire that is shaped into a curved portion 0104 by heat treatment. The head of the curved needle 0101 is a sharp tip formed by grinding. In an embodiment, the curved portion 0104 has a small angle 0105 opposite to the overall direction of the curved portion 0104 at a distance of 0.5 mm to 2 mm from the distal end of the curved portion 0104. The small angle 0105 facilitates the anchor 0100 penetrating deeper into the tissue when the anchor 0100 is pushed out from the guiding catheter 1300. The fixation end 0102 is a proximal end of the curved needle 0101 for fixation, which can be formed by welding, or by winding the proximal end of the curved needle into a twist. In an embodiment, referring to FIG. 5, a binder 0112 is provided on the outside of the fixation end 0102. In an embodiment, the binder 0112 is a metal annular sleeve with a length of 0.5 mm to 3 mm, and the inner wall thereof is in tight contact with the fixation end 0102. In another embodiment, referring to FIG. 6, the binder 0112 is a screw fastener, and the screw fastener is formed by a metal wire that is tightly wound against the fixation end 0102 in the axial direction. In an embodiment, the anchor 0100 also includes a connecting end 0103 of the curved needle. The connecting end 0103 is the connection position of the anchor 0100 that is connected to the anchor push member 1800, and is configured to control the activity of the anchor 0100. In an embodiment, the connecting end 0103 is a circular structure formed by bending the proximal end of curved needle 0101.

Figure 7:
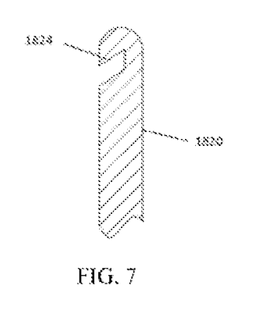
FIG. 7 is a schematic view of an embodiment of a distal end of an anchor push member of the controllable guiding device for the implantable apparatus of the present application.
Figure 8:
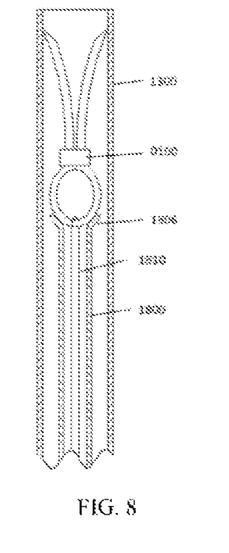
FIG. 8 is a schematic view of an embodiment of a connection between the anchor and the anchor push member.

The anchor push member 1800 is configured to push the anchor 0100 out from the guiding catheter 1300, has adequate strength and toughness, and a distal end portion thereof can be deformed to conform to the bending of the distal end portion of the guiding catheter 1300. The anchor push member 1800 is a thin rod or a filamentary structure made of metal material or shape-memory alloy material. In an embodiment, referring to FIG. 7, a distal end 1820 of the anchor push member 1800 has a fixing hook 1824, configured for detachable connection with the connecting end 0103 of the anchor 0100, thereby limiting the movement of the anchor 0100 and increasing the safety of the product. In another embodiment, referring to FIG. 8, the anchor push member 1800 is made from a stainless steel metal tube with slits formed on the distal end portion thereof in order to conform to the bending and deformation of the guiding catheter 1300. In an embodiment, a pull wire 1810 is provided inside the stainless steel metal tube. The pull wire 1810 passes through the connecting end 0103 of the anchor 0100, being folded in the stainless steel metal tube. The proximal end extends out from the body and can be manipulated manually. In an embodiment, the distal end of the stainless steel metal tube includes a flexible section 1806. The connecting end 0103 of the anchor 0100 is partially located in the area defined by the flexible section 1806, which facilitates the recovery of the anchor 0100 into the guiding catheter 1300.

The anchor 0100 and the distal end portion of the anchor push member 1800 are assembled inside the guiding catheter 1300, respectively. The distance between the distal end of the anchor 0100 and the distal end of the guiding catheter 1300 is in a range from 0.5 mm to 5 mm, which prevents the distal end of the anchor 0100 from being exposed out from the guiding catheter 1300 to affect the anchoring due to releasing or retracting of the guiding catheter 1300. Referring to FIG. 2, a proximal end of the anchor push member 1800 is connected to a fourth controller 1540 of the control handle 1500.

Figure 9:
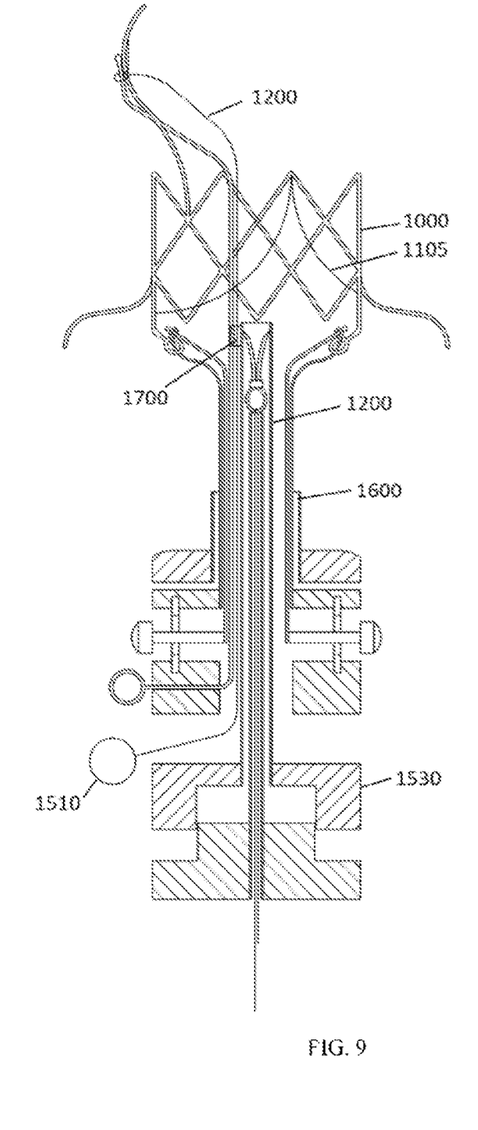
FIG. 9 to FIG. 11 are schematic operational views of the controllable guiding device for the implantable apparatus of the present application.

Referring to FIG. 9, in the assembled state, the distal end of the position-limiting wire 1200 first extends through the guiding hole of the guiding member 1700. The guiding member 1700 can slide along the position-limiting wire 1200. The guiding catheter 1300 is located below the implantable apparatus 1000, leaving the space for the main body of the implantable apparatus 1000. On the one hand, it can reduce damage to the implantable apparatus 1000, especially the prosthetic valve leaflet 1105, during assembling and retracting of the guiding catheter 1300, and on the other hand, it can greatly reduce the diameter of the delivery catheter 1600, improving the performance of the delivery device. Especially, it plays a disruptive role to the surgical approach, such as changing the approach from heart apical or atrial to vascular, reducing the damage to the patient during puncture in the interventional treatment, reducing the surgical risk, and increasing the safety of product.

Referring to FIG. 9, FIG. 2 and FIG. 4A, when the first controller 1510 and the third controller 1530 are moved by manipulating the control handle 1500, the guiding catheter 1300 is guided by the guiding member 1700 and moved axially along the position-limiting wire 1200 toward the distal end, and the distal end portion of the guiding catheter 1300 is bent and deformed. The guiding catheter 1300 pushes the member to be anchored 1102 of the implantable apparatus 1000 to move radially until the position-limiting wire 1200 is tightened, at what time the distal end of the guiding catheter 1300 forms a fixed angle 1301, and the distal end of the guiding catheter 1300 is in contact with the member to be anchored 1102 of the implantable apparatus 1000. During this process, the functions of the position-limiting wire 1200 are as follows: 1. The position-limiting wire 1200 acts as a guide rail to guide and restrict moving of the guiding catheter 1300 along a specific direction, which has following advantages: On the one hand, the position requirement of the guiding catheter 1300 in assemblage is reduced, the difficulty of assemblage is reduced, and the guiding catheter 1300 and the position-limiting wire 1200 are movably connected. There is no internal stress between the various parts, reducing damage to the product. On the other hand, if the anchoring position or anchoring effect is not desired, the guiding catheter 1300 can be withdrawn from the delivery catheter 1600 and reloaded with the anchor 0100, and then a re-anchor operation can be performed along the position-limiting wire 1200, greatly avoiding the surgical risk. 2. The position-limiting wire 1200 acts as a bending wire to change the distal end portion of the guiding catheter 1200 from the initial straight state to the state having the fixed angle, changing the direction of anchor, which is conducive to achieving a desired anchoring position and simplifies the structure of the delivery device. 3. The position-limiting wire 1200 acts as a positioning wire, which is connected to a specific position of the implantable apparatus 1000 to accurately control the position of the anchor outlet of the guiding catheter 1300 relative to the member to be anchored 1102 to achieve precise anchoring. 4. The position-limiting wire 1200 acts as a pull wire to offset the interacting force between the anchor 0100 and the member to be anchored 1102 during the anchoring operation and to ensure that the guiding catheter 1300 is in tight contact with the member to be anchored 1102 before anchoring of the anchor 0100, ensuring that the anchor 0100 safely and effectively fixes the member to be anchored 1102 to the target tissue. 5. The position-limiting wire 1200 acts as a detachable wire, which can be separated from the implantable apparatus 1000 after the anchoring operation is completed.

The implantable apparatus 1000 is provided with a connecting ring 1110, and the connecting ring 1110 can be disposed at the end of the implantable apparatus 1000 or at other positions of the implantable apparatus 1000, so that a suitable anchoring position can be selected according to actual needs, and a wide application range can be achieved.

Figure 10:
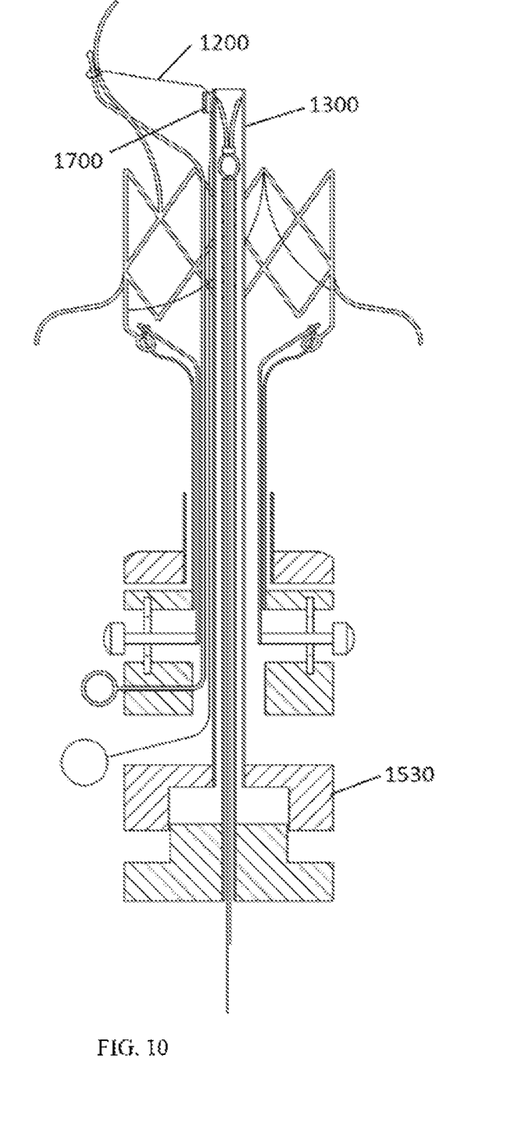
Figure 11:
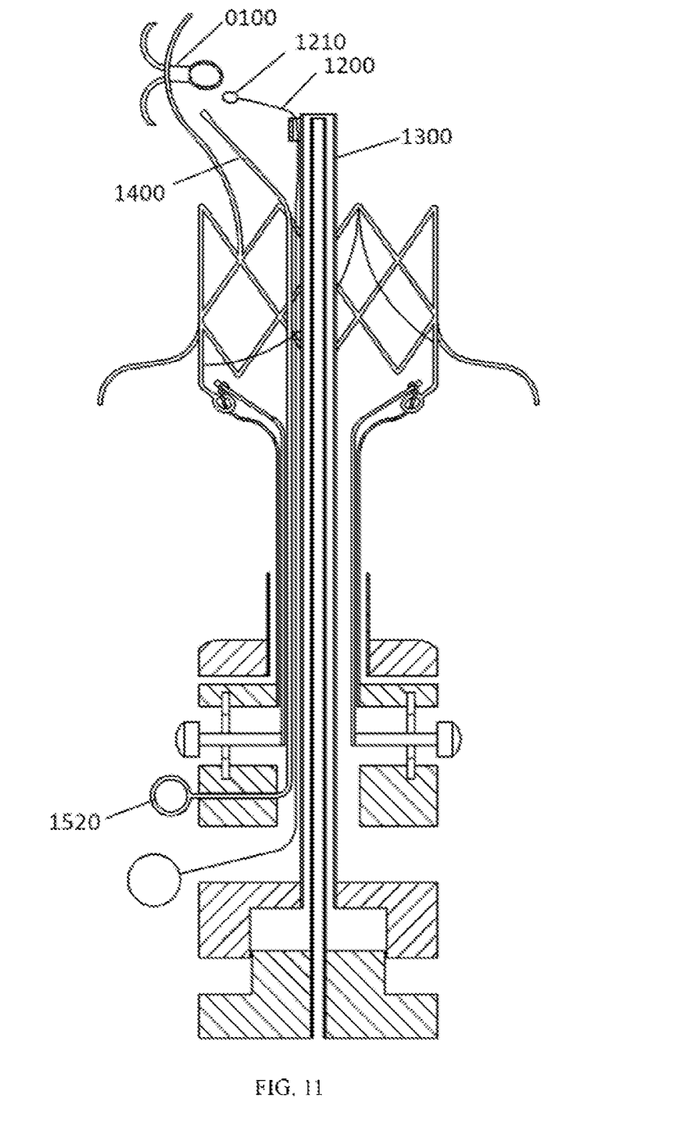

In the surgical operation, referring to FIG. 9, the implantable apparatus 1000 is first released from the delivery catheter 1600 to a preliminary position, and the control handle 1500 is manipulated to move the first controller 1510 toward the proximal end, thereby tightening the position-limiting wire 1200. Referring to FIG. 10, the control handle 1500 is manipulated to move the third controller 1530, thereby moving the guiding catheter 1300 along the position-limiting wire 1200 in the axial direction toward the distal end under the guidance of the guiding member 1700. The distal end portion of the guiding catheter 1300 is bent and deformed. By pulling tight and lock the position-limiting wire 1200, as shown in FIG. 2, the distal end portion of the guiding catheter 1300 forms a fixed angle 1301, and the distal end of the guiding catheter 1300 abuts against the member to be anchored 1102 of the implantable apparatus 1000. A fixed connection is formed among the member to be anchored 1102 of the implantable apparatus 1000, the position-limiting wire 1200, the control rod 1400, and the guiding catheter 1300. At this time, the control rod 1400 and the guiding catheter 1300 are respectively in tight contact with the member to be anchored 1102 of the implantable apparatus 1000, and located at both ends of the connecting ring 1110. The distance between the end of the guiding member 1700 and the distal end of the locking ring 1210 is approximately equal to the diameter of the connecting ring 1110. The member to be anchored 1102 of the implantable apparatus 1000 fits tight with the control rod 1400 and the guiding catheter 1300, and has no room for movement relative to the control rod 1400 and the guiding catheter 1300. The fourth controller 1540 of the control handle 1500 is manipulated to make the anchor push member 1800 push the anchor 0100 to move along the guiding catheter 1300 toward the distal end, and the anchor 0100 is gradually released from the guiding catheter 1300 to deploy. The tip of the anchor 0100 first passes through the member to be anchored 1102, and then punctures the target tissue, so that the anchor 0100 fixes the member to be anchored 1102 of the implantable apparatus 1000 to the target tissue. Whether or not the anchor 0100 has been anchored to the target tissue can be verified through a medical imaging device. If not, the pull wire 1810 is pulled to withdraw the anchor 0100 into the guiding catheter 1300, re-adjust the position of the implantable apparatus 1000, and then perform the anchoring operation again. When the anchoring operation is completed, the pull wire 1810 is pulled out from the anchor push member 1800. Referring to FIG. 11, when the anchoring operation is completed, the control handle 1500 is manipulated to move the second controller 1520 in the axial direction to withdraw the distal end of the control rod 1400 from the locking ring 1210. The connection among the member to be anchored 1102, the position-limiting wire 1200, the control rod 1400, and the guiding catheter 1300 is released, and the release of the member to be anchored 1102 of the implantable apparatus 1000 is completed. Finally, the sixth controller 1560 of the control handle 1500 is manipulated to move the control member 1910 toward the proximal end until the distal end of the control member 1910 is withdrawn from the ring at the distal end of the connecting member 1900, thereby completely releasing the implantable apparatus 1000 from the delivery catheter 1600. The delivery catheter 1600 is then withdrawn from the heart, and the implantable apparatus 1000 is anchored to the target tissue via the anchor 0100.

The device of the present application is easy to disassemble, the member to be anchored 1102 of the implantable apparatus 1000 can be separated from the delivery system quickly, and the controllable guiding device no longer affects the implantable apparatus 1000 after disassembling, thereby reducing the surgical risk.

The technical features of the above-described embodiments may be arbitrarily combined. In order to make the description simple, not all possible combinations of the technical features in the above embodiments are described. However, as long as there is no contradiction in the combination of these technical features, the combinations should be in the scope of the present application.

What described above are only several embodiments of the present application, and these embodiments are specific and detailed, but not intended to limit the scope of the present application. It should be understood by one ordinary skill in the art that various modifications and improvements can be made without departing from the conception of the present application, and all fall within the protection scope of the present application. Therefore, the patent protection scope of the present application is defined by the appended claims.

What is claimed is:

1. A controllable guiding device for an implantable apparatus, comprising the implantable apparatus, a delivery catheter, and a control handle, characterized by further comprising a guiding catheter and a position-limiting wire,
    wherein the implantable apparatus comprises a member to be anchored, the position-limiting wire is detachably connected to the implantable apparatus, a proximal end of the position-limiting wire is connected to the control handle, a distal end of the guiding catheter is provided with a guiding member, a distal end portion of the guiding catheter is bendable, a proximal end of the delivery catheter and a proximal end of the guiding catheter are respectively connected to the control handle;
    in an assembled state, the guiding catheter and the position-limiting wire are placed in the delivery catheter, the position-limiting wire extends through the guiding member;
    on a condition that the control handle is manipulated to make the guiding member on the guiding catheter move along the position-limiting wire toward the distal end, the distal end portion of the guiding catheter is bent and deformed, such that the distal end of the guiding catheter abuts against the member to be anchored of the implantable apparatus.

2. The controllable guiding device for the implantable apparatus according to claim 1, further comprising an anchor and an anchor push member, wherein in the assembled state, the anchor and the anchor push member are placed in the guiding catheter; on a condition that the anchor push member pushes the anchor, the anchor moves toward the distal end to anchor the member to be anchored of the implantable apparatus to a target tissue.

3. The controllable guiding device for the implantable apparatus according to claim 1, further comprising a control rod, wherein a distal end of the position-limiting wire has a locking ring, the implantable apparatus comprises a connecting ring, a proximal end of the control rod is connected to the control handle;
    in the assembled state, a distal end of the control rod is inserted into the locking ring passed through the connecting ring of the implantable apparatus;
    on a condition that the control handle is manipulated to tighten and lock the position-limiting wire, a connection is formed between the implantable apparatus, the position-limiting wire, the control rod, and the guiding catheter, thereby fixing the relative position therebetween;
    on a condition that the control handle is manipulated to axially move the control rod, such that the distal end of the control rod is disengaged from the locking ring, the implantable apparatus is releasable from the position-limiting wire.

4. The controllable guiding device for the implantable apparatus according to claim 3, wherein the distal end of the control rod is a detach-preventing end, the detach-preventing end is an inverted conical structure, a Y-shaped structure, a wave-shaped structure, or a compressible round structure.

5. The controllable guiding device for the implantable apparatus according to claim 3, wherein the guiding member is fixedly connected to the guiding catheter, the guiding member is located at the distal end of the guiding catheter, the guiding member comprises a guiding hole;

in the assembled state, the distal end of the position-limiting wire first extends through the guiding hole, and then extends through the connecting ring.

6. The controllable guiding device for the implantable apparatus according to claim 5, wherein the guiding member and the guiding catheter are integrated together as one piece.

7. The controllable guiding device for the implantable apparatus according to claim 5, wherein the control rod extends through the guiding hole in the guiding member.

8. The controllable guiding device for the implantable apparatus according to claim 3, wherein the connecting ring is disposed at an end of the implantable apparatus.

9. The controllable guiding device for the implantable apparatus according to claim 1, wherein the member to be anchored is integrated with the implantable apparatus.

10. The controllable guiding device for the implantable apparatus according to claim 1, wherein the member to be anchored is a flexible piece, one end of the member to be anchored is connected to the implantable apparatus.

11. The controllable guiding device for the implantable apparatus according to claim 1, wherein the member to be anchored comprises a support mesh.

12. The controllable guiding device for the implantable apparatus according to claim 1, further comprising a connecting member and a control member placed in the delivery catheter, wherein the implantable apparatus further comprises an annular coupling end, the connecting member is a rod-shaped structure whose distal end has a ring; in the assembled state, a distal end of the control member passes through the ring of the connecting member passed through the annular coupling end, a proximal end of the control member is fixedly connected to the control handle.

13. The controllable guiding device for the implantable apparatus according to claim 1, wherein the implantable apparatus further comprises a frame, the frame is a compressible structure, the member to be anchored is disposed in the space formed by the frame.

14. The controllable guiding device for the implantable apparatus according to claim 1, further comprising a second position-limiting wire and a second guiding member, the guiding member and the second guiding member are symmetrically arranged at the distal end of the guiding catheter, the position-limiting wire and the second position-limiting wire respectively extend through the guiding member and the second guiding member; on a condition that the position-limiting wire and the second position-limiting wire are tightened, the distal end of the guiding catheter is self-positioned to a midline of the member to be anchored.

15. The controllable guiding device for the implantable apparatus according to claim 1, wherein in the assembled state, the guiding catheter is located next to the implantable apparatus along an axial direction.

\* \* \* \* \*